(12) United States Patent
Rathbun

(10) Patent No.: US 10,874,497 B2
(45) Date of Patent: Dec. 29, 2020

(54) FORCE ACTUATED GRIPPING DEVICE FOR AN IMPLANTABLE PROSTHESIS

(71) Applicant: C.R. Bard, Inc., Murray Hill, NJ (US)

(72) Inventor: Tami L. Rathbun, Exeter, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 115 days.

(21) Appl. No.: 15/560,607

(22) PCT Filed: Mar. 25, 2016

(86) PCT No.: PCT/US2016/024176
§ 371 (c)(1),
(2) Date: Sep. 22, 2017

(87) PCT Pub. No.: WO2016/154523
PCT Pub. Date: Sep. 29, 2016

(65) Prior Publication Data
US 2018/0049857 A1    Feb. 22, 2018

Related U.S. Application Data

(60) Provisional application No. 62/176,885, filed on Mar. 26, 2015.

(51) Int. Cl.
*A61F 2/00*       (2006.01)
*A61B 17/122*     (2006.01)

(52) U.S. Cl.
CPC ........ *A61F 2/0063* (2013.01); *A61B 17/1227* (2013.01); *A61F 2002/0068* (2013.01);
(Continued)

(58) Field of Classification Search
CPC ......... A61B 17/1227; A61F 2002/0068; A61F 2220/0008; A61F 2220/0016;
(Continued)

(56) References Cited

U.S. PATENT DOCUMENTS 2,339,187 A      1/1944   Pain
2,513,846 A *    7/1950   Collins ................. A47K 10/14
                                              248/314

(Continued)

FOREIGN PATENT DOCUMENTS

CN        1765314 A       5/2006
CN      102772829 A      11/2012
(Continued)

OTHER PUBLICATIONS

EP 16769757.2, Nov. 19, 2018, Extended Eurpoean Search Report.
(Continued)

*Primary Examiner* — Mohamed G Gabr
(74) *Attorney, Agent, or Firm* — Wolf, Greenfield & Sacks, P.C.

(57) ABSTRACT

A prosthesis for securing to soft tissue includes a surgical mesh layer and a tissue gripping layer having a tissue gripping element. The surgical mesh layer is attached to the tissue gripping layer. The tissue gripping element may include a primary opening and one or more slits. Tabs defined between pairs of adjacent slits may be moveable relative to the pre-actuation position of the primary opening and/or relative to the surgical mesh layer.

24 Claims, 16 Drawing Sheets

(52) U.S. Cl.
CPC ........... *A61F 2220/0008* (2013.01); *A61F 2220/0016* (2013.01); *A61F 2230/005* (2013.01); *A61F 2230/0006* (2013.01); *A61F 2230/0019* (2013.01)

(58) Field of Classification Search
CPC ...... A61F 2230/0006; A61F 2230/0019; A61F 2230/005; A61F 2/0063; A61F 2/0045
See application file for complete search history.

(56) References Cited

U.S. PATENT DOCUMENTS

| | | | |
|---|---|---|---|
| 3,099,855 | A | 8/1963 | Nash |
| 6,280,453 | B1 | 8/2001 | Kugel et al. |
| 6,610,006 | B1 | 8/2003 | Amid et al. |
| 8,298,290 | B2 | 10/2012 | Pelissier et al. |
| 2003/0163160 | A1* | 8/2003 | O'Malley ............ A61B 17/08 606/213 |
| 2006/0090279 | A1 | 5/2006 | Nishinaka et al. |
| 2009/0281568 | A1 | 11/2009 | Cendan et al. |
| 2012/0253362 | A1* | 10/2012 | Noda ............ A61B 17/12013 606/140 |
| 2013/0218125 | A1 | 8/2013 | Stopek et al. |
| 2014/0025093 | A1 | 1/2014 | Horton et al. |
| 2014/0194679 | A1* | 7/2014 | Sjoquist ............ A61F 2/0045 600/37 |

FOREIGN PATENT DOCUMENTS

| | | |
|---|---|---|
| CN | 103251462 A | 8/2013 |
| JP | 2013-165966 A | 8/2013 |
| WO | WO 2006/034117 A1 | 3/2006 |
| WO | WO 2009/075786 A1 | 6/2009 |
| WO | WO 2009/111802 A1 | 9/2009 |
| WO | WO 2011/063412 A2 | 5/2011 |
| WO | WO 2011/063412 A3 | 5/2011 |
| WO | WO 2014/139633 A1 | 9/2014 |
| WO | WO 2015/011417 A1 | 1/2015 |
| WO | WO 2017/066458 A1 | 4/2017 |

OTHER PUBLICATIONS

International Search Report and Written Opinion dated Jun. 13, 2016 in connection with International Application No. PCT/US2016/024176.
Extended European Search Report dated Nov. 19, 2018 in connection with European Application No. 16769757.2
PCT/US2016/024176, Jun. 13, 2016, International Search Report and Written Opinion.
European Communication dated Feb. 4, 2020 in connection with European Application No. 16 769 757.2.

* cited by examiner

FORCE ACTUATED GRIPPING DEVICE FOR AN IMPLANTABLE PROSTHESIS

RELATED APPLICATIONS

This Application is a 35 U.S.C. § 371 U.S. National Stage application of International Application No. PCT/US2016/024176, filed Mar. 25, 2016, which claims the benefit priority under 35 U.S.C. § 119(e) of U.S. Provisional Application Ser. No. 62/176,885, filed on Mar. 26, 2015, the entire contents of each of which are incorporated herein by reference.

FIELD

Aspects relate to a force actuated gripping device for temporarily or permanently securing an implantable prosthesis to soft tissue, to an implantable prosthesis incorporating a force actuated gripping device, and to methods for using such a force actuated gripping device and an implantable prosthesis incorporating same.

BACKGROUND

An implantable prosthesis, for example a surgical mesh, may be used to repair a soft tissue defect such as a hernia. The surgical mesh, typically in the form of a patch, a plug, or a combination patch and plug, may be implanted through an open procedure, a minimally invasive procedure (e.g., laparoscopic), or through a hybrid open and minimally invasive technique. In some procedures, sutures or fasteners, such as staples or tacks, may be deployed through the surgical mesh into tissue to secure the surgical mesh in place. It also is known to embed microfilaments or barbs that protrude from the surgical mesh into tissue to temporarily or permanently anchor the prosthetic in place relative to the defect.

SUMMARY

According to one aspect, a prosthesis that is securable to soft tissue includes a surgical mesh and a tissue gripping element that is constructed and designed to grip soft tissue to attach the surgical mesh to the soft tissue. The tissue gripping element is attached to the surgical mesh. The tissue gripping element includes a base and a first slit formed through the base. The slit is defined by at least two portions of the base. In response to an application of force to actuate the tissue gripping element, tissue is gripped between the at least two portions of the base.

According to another aspect, a pressure actuated body tissue gripping element for an implantable prosthesis includes a base and a first slit formed through the base. The slit is defined by at least two portions of the base. The tissue gripping element is sterilized and implantable and is constructed and designed to grip soft tissue.

According to another aspect, a method of securing prosthesis to soft tissue includes positioning the prosthesis at an implantation site of a human or animal body. The prosthesis includes a tissue gripping element attached to surgical mesh. The method further includes placing the tissue gripping element adjacent to tissue to which the prosthesis is to be attached to. The method also includes applying a mechanical force to actuate the tissue gripping element of the tissue gripping layer to grip the tissue.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. Various embodiments of the invention will now be described, by way of example, with reference to the accompanying drawings, in which.

DETAILED DESCRIPTION

Figure 1:
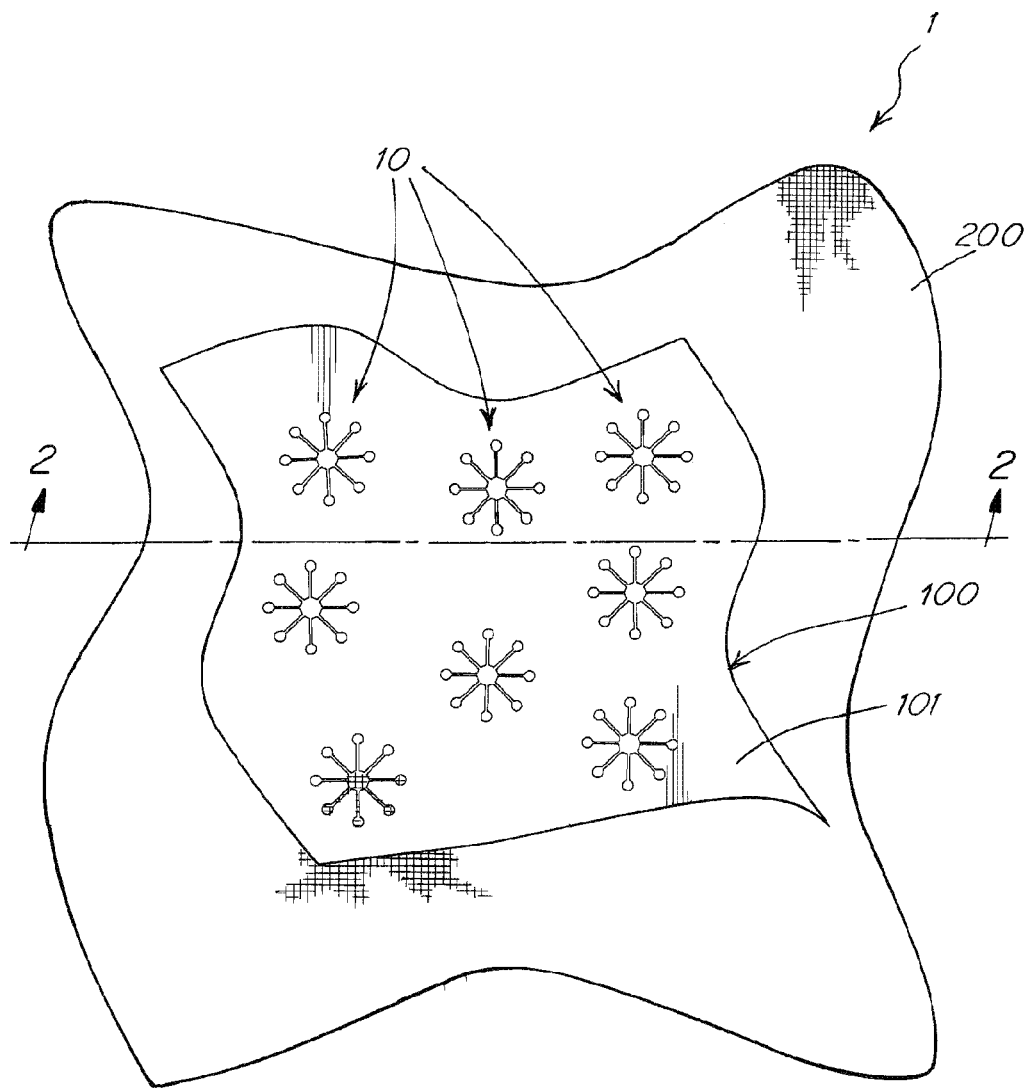
FIG. 1 is an illustration of a prosthesis for repairing a soft tissue defect, the prosthesis including a tissue gripping layer attached to a substrate, such as a surgical mesh layer.

It should be understood that aspects of the invention are described herein with reference to certain illustrative embodiments and the figures. The illustrative embodiments described herein are not necessarily intended to show all aspects of the invention, but rather are used to describe a few illustrative embodiments. Thus, aspects of the invention are not intended to be construed narrowly in view of the illustrative embodiments. In addition, it should be understood that aspects of the invention may be used alone or in any suitable combination with other aspects of the invention.

Various embodiments are described in connection with a force actuated gripping device for securing an implantable prosthesis to soft tissue. The prosthesis may be configured for soft tissue repair, reconstructive surgery (e.g., breast reconstruction or augmentation), or any other procedure. In some embodiments, the prosthesis may be a patch, a plug, or a combination patch and plug, that is indicated for chest or abdominal wall reconstruction and augmentation, or hernia repair including, but not limited to, repair of a groin hernia (e.g., indirect inguinal hernia, direct inguinal hernia, femoral hernia), a ventral hernia (e.g., umbilical hernia, incisional hernia), a hiatal hernia, a parastomal hernia, an epigastric hernia, or a paraesophageal hernia. Although the force actuated gripping device is described particularly in connection with a hernia repair prosthetic, the invention is not necessarily so limited, and may be employed with other implantable prosthetics, as well as may be used in other surgical or medical treatments. For ease of understanding, the hernia prosthesis is described in connection with a laparoscopic procedure but may be employed in other minimally invasive procedures, in an open procedure, a hybrid open and minimally invasive procedure, or in other techniques for repairing a hernia or other soft tissue defect as should be apparent to one of skill in the art.

A prosthesis for repairing a hernia may include a prosthesis body having a first side that will be positioned against a tissue or muscle wall, such as the abdominal wall, that includes the defect. The first side of the prosthesis body may be configured for tissue ingrowth; for example, it may be in the form of a surgical mesh. Where a second side of the prosthesis body may be located adjacent sensitive organs or other area of potential adhesion with the prosthetic, the second side of the prosthesis body may include a barrier, such as a layer of barrier material, or a barrier coating, to prevent adhesions between the first side of the prosthesis and the sensitive organs.

In a minimally invasive technique, as well as in certain open procedures, a hernia prosthesis, such as a hernia repair patch, may be reduced in size to facilitate delivery of the prosthetic device to the treatment site. For example, in a laparoscopic procedure, a hernia repair prosthesis may be rolled into a slender cylindrical shape, or otherwise collapsed into a smaller configuration, suitable for passage through a narrow cannula or other access to the surgical site, which may have an inner diameter of approximately 10 mm, of approximately 5 mm, or of even a finer size. After delivery, the reduced hernia prosthesis is transformed into an expanded configuration. The expanded prosthesis is then placed about the hernia defect and may be fixated to the abdominal wall to secure the prosthetic to tissue. In some embodiments, tissue integration with the implantable prosthetic secures the prosthetic in place.

Applicant has recognized a need for a soft tissue repair prosthesis that can be attached to tissue quickly and easily, and which will maintain the prosthetic in place pending adequate tissue integration. Applicant has also appreciated that, in certain embodiments, further including a reinforcing structure in the prosthesis may help to facilitate expansion of the reduced prosthetic upon arrival at the implantation site.

According to one aspect, the prosthesis includes tissue gripping elements that can be force-actuated to attach to soft tissue. It should be appreciated that the tissue gripping elements may be used in various arrangements. For example, in some embodiments, the tissue gripping elements may extend, directly or indirectly, from a substrate of a medical device. For example, and without limitation, the substrate may be a surgical mesh and the medical device may be a hernia repair patch or plug. In another illustrative example, the tissue gripping elements may be associated with a substrate, such as a surface or other layer, of a breast implant so as to secure the breast implant in place at the treatment site.

In some embodiments, a prosthesis 100 includes a surgical mesh layer 200 and a tissue gripping layer 100 as shown in FIG. 1. The tissue gripping layer 100 has a base 101 and includes a plurality of tissue gripping elements. It should be understood that the unbounded shapes of the layers 100, 200 indicate that the layers 100, 200 may be larger than what is shown in the figures and may have any outline shape. In addition, although the prosthesis is shown generally as planar (including slight convexity, concavity, combined convexity and concavity), in some embodiments, the surgical mesh layer and/or the tissue gripping layer may have a three-dimensional shape (e.g., cylindrical or conical plug). The surgical mesh layer may be larger than, substantially equal to, or smaller than that of the tissue gripping layer 100. In some embodiments, the tissue gripping layer is significantly smaller than the surgical mesh layer.

Figure 2:
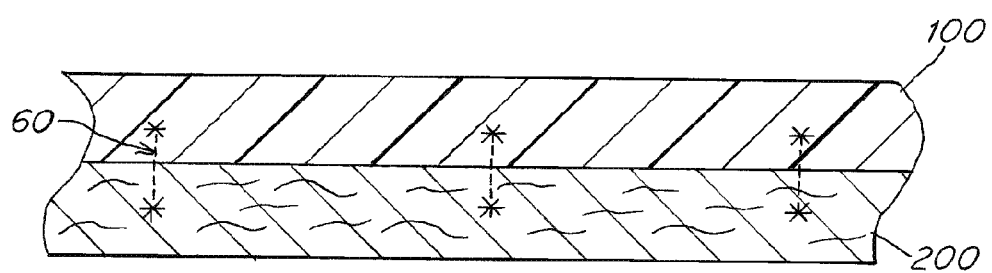
FIG. 2 is a cross-sectional view of the prosthesis shown in FIG. 1 taken along line 2-2.

In some embodiments, the tissue gripping layer is attached to the surgical mesh layer. FIG. 2 depicts a cross-sectional view of the prosthesis through line 2-2 of FIG. 1. As seen in FIG. 2, one or more stitches 60 attach the tissue gripping layer 100 to the surgical mesh layer 200. It should be understood that the thicknesses of the layers shown are for schematic purposes only and are not to scale. The thickness of the surgical mesh layer 200 may be larger than, substantially equal to, or smaller than that of the tissue gripping layer 100. The surgical mesh and the tissue gripping film may be attached to one another via various different arrangements. The surgical mesh may be mechanically attached to the tissue gripping film, such as by stitches, sutures, staples, fasteners, and the like. The tissue gripping film may include small holes or openings to receive such stitches, sutures, staples or fasteners. The tissue gripping film may be welded onto and/or into the surgical mesh. The tissue gripping film may be molded into the surgical mesh using multiple layers of surgical mesh and then die cut as a second operation. The tissue gripping film and the surgical mesh may be attached together via adhesive, photochemical reaction, ultraviolet curing, welding, or by any other suitable arrangement.

It should be understood that, while the surgical mesh layer and tissue gripping layer are shown in the figures as being superimposed on top of one another, in other embodiments, a surgical mesh region and a tissue gripping region may be arranged side-by-side in a single layer. It is contemplated that the surgical mesh layer and the tissue gripping layer could be substantially co-planar. All discussions regarding a "surgical mesh layer" and a "tissue gripping layer" include embodiments where the two layers are contained within the same layer or plane.

Figure 3:
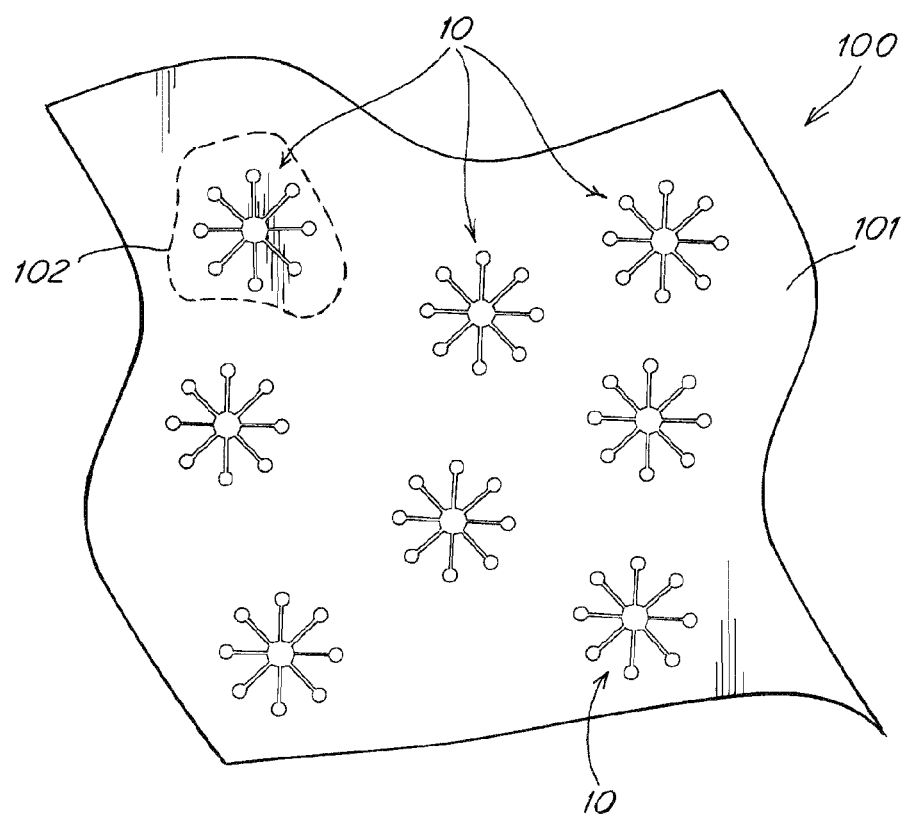
FIG. 3 is an illustration of a tissue gripping layer having a plurality of tissue gripping elements.

The tissue gripping elements of the tissue gripping layer will now be discussed in more detail. As seen in FIG. 3, a tissue gripping layer 100 includes a base 101 and may have a plurality of tissue gripping elements 10. In some embodiments, however, a tissue gripping layer has only one tissue gripping element. Region 102 of the tissue gripping layer 100 in FIG. 3 is enlarged and depicted in FIG. 4 to illustrate the tissue gripping element 10 in more detail. In some embodiments, such as that illustrated in FIG. 4, the tissue gripping element 10 includes a plurality of slits 30 formed through the base 101 of the tissue gripping layer. A tab 50 is defined between each pair of adjacent slits. In some embodiments, the tab is a cantilevered tab. In some embodiments, the tissue gripping element includes a primary opening 20 formed through the base 101 of the tissue gripping layer prior to actuation of the tissue gripping element, as in the embodiment shown in FIG. 4. Prior to actuation of the tissue gripping element, at least a portion of the perimeter of the primary opening 20 may be bounded by the end(s) of tab(s) 50. In such embodiments, actuation of the tissue gripping element will cause one or more of the tabs 50 to move away from the base 101, which may further expand the size of the primary opening 20. In one embodiment, a tissue gripping element includes only a single slit where tissue may be gripped between the two or more portions of the tissue gripping element defining the slit.

In other embodiments, movement of one or more tabs away from the base reveals a primary opening formed through the base. For example, in some embodiments, the ends of the tabs may be coincident at a common point such that there is no opening at the ends of the tabs or formed between the ends of the tabs. Upon actuation of such a tissue gripping element, one or more of the tabs will move, revealing a primary opening through the base. As will be discussed in more detail in a later section, the tabs are moveable relative to the base of the tissue gripping element, the surgical mesh layer and/or relative to the pre-actuation position of the primary opening. The primary opening, then, may have a variable shape that may change in response to forces applied to the tissue gripping element.

In some embodiments, the tissue gripping element includes one or more relief openings 40. Each slit 30 has a first end 32 and a second end 34. In some embodiments, the primary opening 20 is positioned at the first end 32 of the slit 30 and a relief opening 40 is positioned at the second end 34 of the slit 30. Without wishing to be bound by theory, positioning a relief opening at an end of the slit may serve to prevent the slit from propagating through the tissue gripping layer in response to forces applied to the gripping element. The relief opening may help to increase the durability of the tissue gripping layer and help maintain the integrity of the layer as the layer is manipulated (e.g. rolled up, folded and/or twisted). In some embodiments, the relief opening is smaller than the primary opening. In other embodiments, the relief opening is substantially the same size as the primary opening, or larger than the primary opening. The relief openings 40 may have the same shape and/or size as one another or may have differing shapes and/or sizes. The relief openings may be circular, elliptical, irregular, or any other suitable shape.

In some embodiments, instead of having the tabs integrally formed with the tissue gripping layer (e.g., where tabs are formed by cutting slits into a sheet of material), tabs are attached to a sheet of material. Tabs may be attached via adhesive, photochemical reaction, ultraviolet curing, welding, ultrasonic welding, or by any other suitable arrangement.

The tissue gripping action of the tissue gripping element will now be described. The tissue gripping elements are constructed and designed to attach to soft tissue. According to one aspect, the tissue gripping elements must be actuated to attach to soft tissue, rather than the tissue gripping elements being pre-actuated. Applicants have recognized that one benefit of avoiding pre-actuated gripping elements is that the gripping elements are less likely to entangle with an associated surgical mesh or other substrate when the patch is reduced in size, such as when rolled up into a slender shape suitable for minimally invasive delivery. The tissue gripping element may grip tissue upon application of force to the prosthesis in a direction that is parallel with the initial movement direction of the tab(s) of the tissue gripping element. When the prosthesis reaches the implantation site, the prosthesis is unfurled and then the tissue gripping layer side of the prosthesis is positioned against tissue surrounding the defect. Force is applied to move the gripping elements to an outwardly extended gripping position, such as by applying a force to the side of the prosthesis opposite the tissue gripping element(s), e.g. via mechanical force, via an instrument contacting the prosthesis and exerting a force on the prosthesis, by hand, by concentrated air pressure directed at the prosthesis, by fluid jet, or by any other suitable means. Force may be applied to one or more small or large regions on the prosthesis. In some embodiments, force may only be applied to the prosthesis at regions where the tissue gripping layer is present. In some embodiments, force may be applied to the prosthesis at regions close to or directly on the tissue gripping elements. As used herein, the "pre-actuation position of the primary opening" refers to the position of the primary opening of the tissue gripping element prior to actuation of the tissue gripping element. In some embodiments, application of pressure onto the prosthesis causes one or more tabs of a tissue gripping element to move relative to the pre-actuation position of the primary opening and/or relative to the surgical mesh layer. In some embodiments, the tabs move in the direction of the applied force. Movement of one or more tabs of the tissue gripping element causes the tissue gripping element to catch and grip tissue. As a result, the tissue gripping element is attached to the tissue. If the prosthesis includes a surgical mesh layer, the tissue gripping element attaches the surgical mesh layer to the tissue. Without wishing to be bound by theory, in some cases, the end, corners/points, and/or the sides of the tabs may catch onto tissue. In some cases, the tabs may include pointed ends, barbs, or other projections that may catch onto tissue. In some cases, tissue may become lodged between tabs, into the slits of the tissue gripping element. In some cases, tissue may be received into and remain within the primary opening. In some cases, tissue may be received into and remain within the relief openings. As discussed above, relief openings at the ends of the slits may serve to prevent the slit from propagating through the tissue gripping layer, especially during movement of the tabs upon application of force to the tissue gripping layer.

Alternatively or in addition, the tissue gripping element may grip tissue upon application of force to tissue to move tissue through the slit(s) of a tissue gripping element.

If desired, the surgeon additionally may use sutures, tacks, staples, other fasteners or other attachment arrangements to further attach the prosthesis in place.

The slits may be positioned in different arrangements on the base. In some embodiments, the slits are positioned and oriented to point toward a reference point. In some embodiments, a primary opening is formed at the reference point. In other embodiments, no primary opening is at the reference point. In some embodiments, the slits are equally spaced about the reference point. For example, the slits may be arranged to have uniform angular spacing about the reference point. In some embodiments, the slits are directed radially outwardly away from the reference point.

Figure 4:
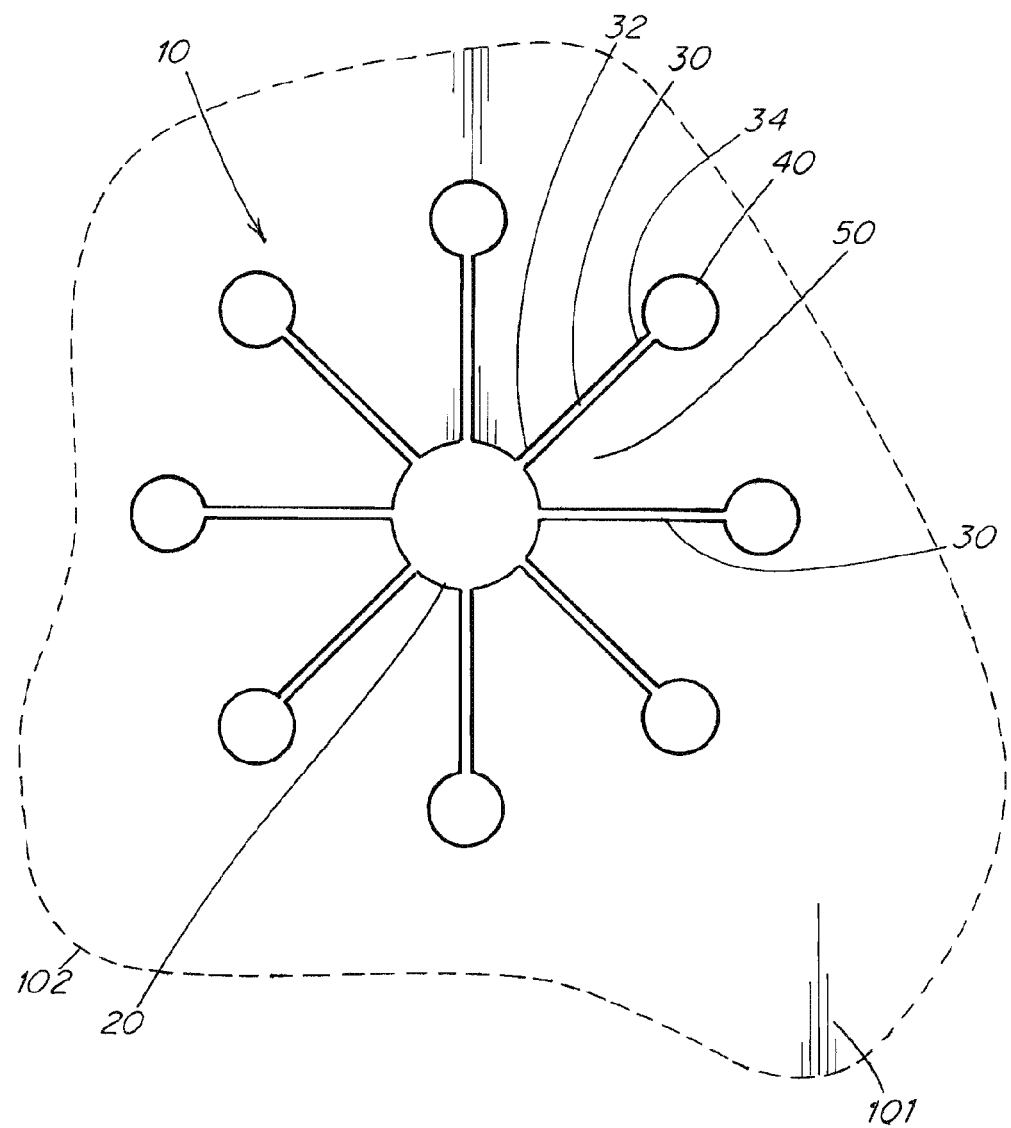
FIG. 4 is an enlarged illustration of a tissue gripping element according to a first embodiment.
Figure 5:
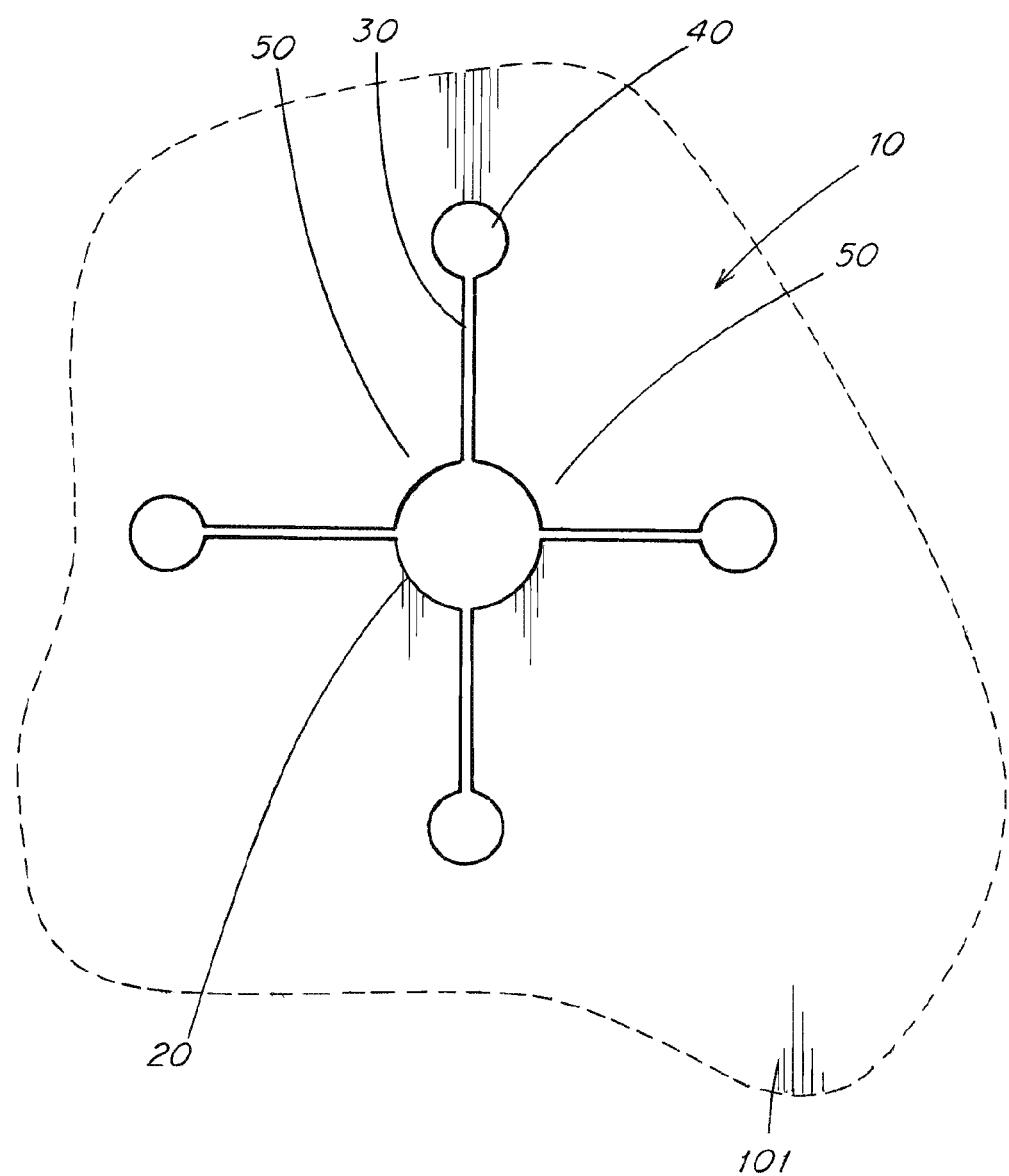
FIG. 5 is an enlarged illustration of a tissue gripping element according to another embodiment.
Figure 6:
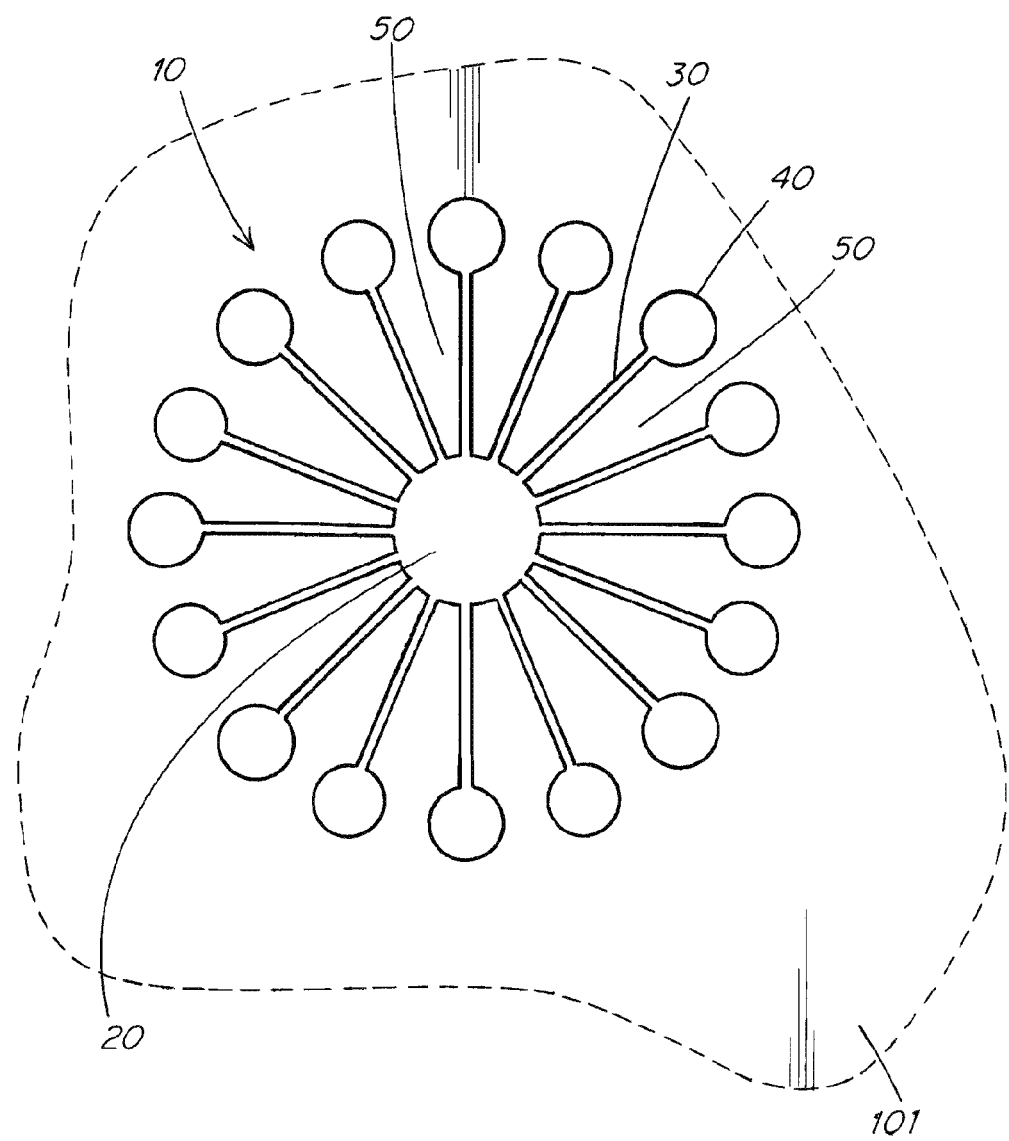
FIG. 6 is an enlarged illustration of a tissue gripping element according to another embodiment.

In the illustrative embodiment shown in FIG. 4, the tissue gripping element 10 includes eight slits 30 extending from the primary opening 20. The embodiment also includes eight tabs 50. However, it should be appreciated that different numbers of slits and tabs may be included in a tissue gripping element. For example, in the illustrative embodiment shown in FIG. 5, the tissue gripping element 10 includes four slits 30 extending from the primary opening 20 and four tabs 50, each tab defined between a pair of adjacent slits. In another illustrative embodiment shown in FIG. 6, the tissue gripping element includes sixteen slits 30 extending from the primary opening 20 and sixteen tabs 50. The tissue gripping element may include any number of slits and/or tabs suitable for the desired application as should be apparent to one of skill in the art.

Figure 7:
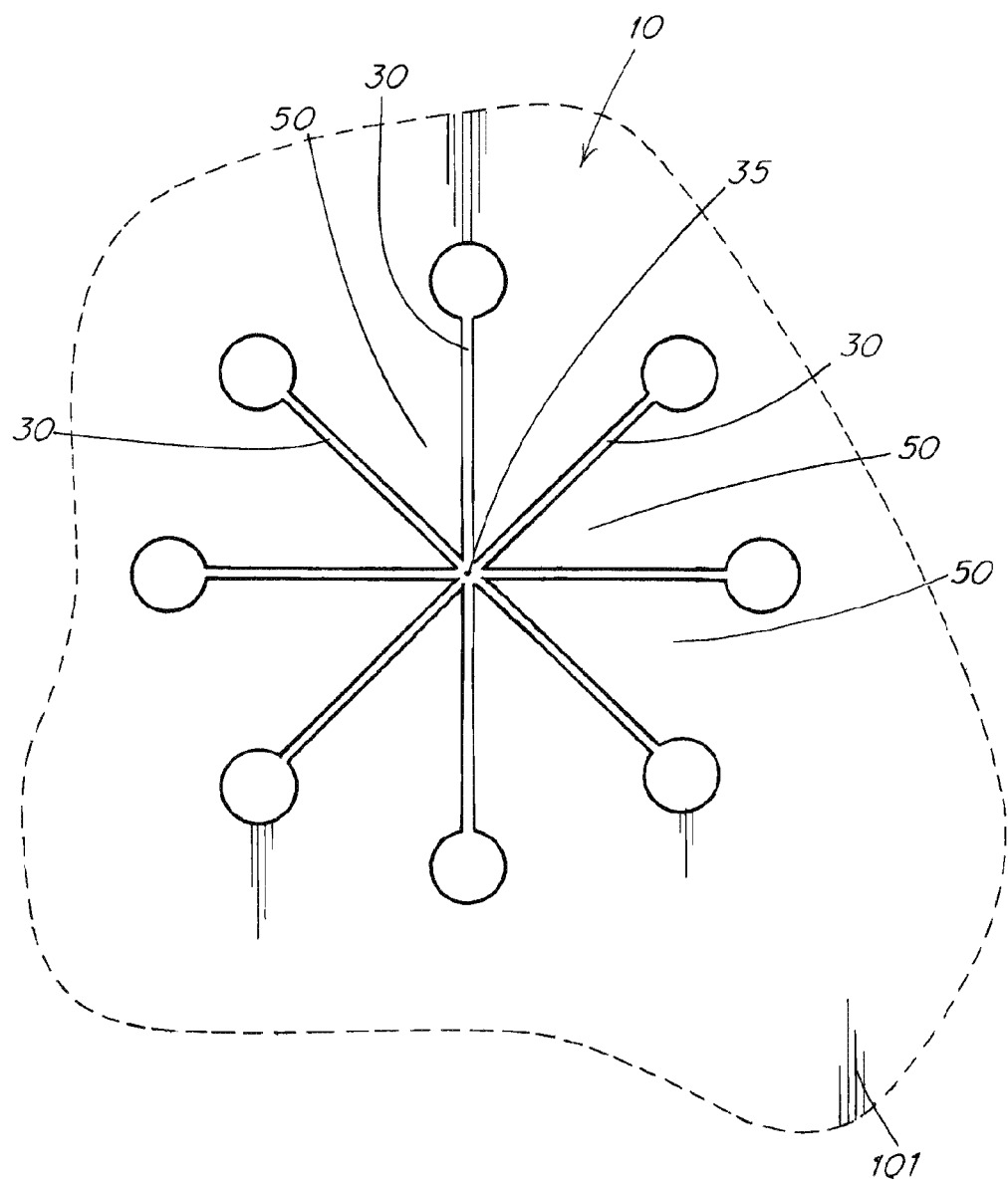
FIG. 7 is an enlarged illustration of a tissue gripping element according to another embodiment.

In the illustrative embodiment shown in FIG. 7, the ends of the tabs 50 are coincident at a common point such that there is no opening at the ends of the tabs or formed between the ends of the tabs prior to actuation of the tissue gripping element 10. Upon actuation of the tissue gripping element 10, however, the tabs 50 will move, revealing a primary opening through the base 101. In the embodiment shown in FIG. 7, slits 30 are positioned and oriented to point toward an imaginary reference point 35. The slits 30 are equally spaced about the reference point 35 and may be directed radially outwardly away from the reference point 35.

Figure 8:
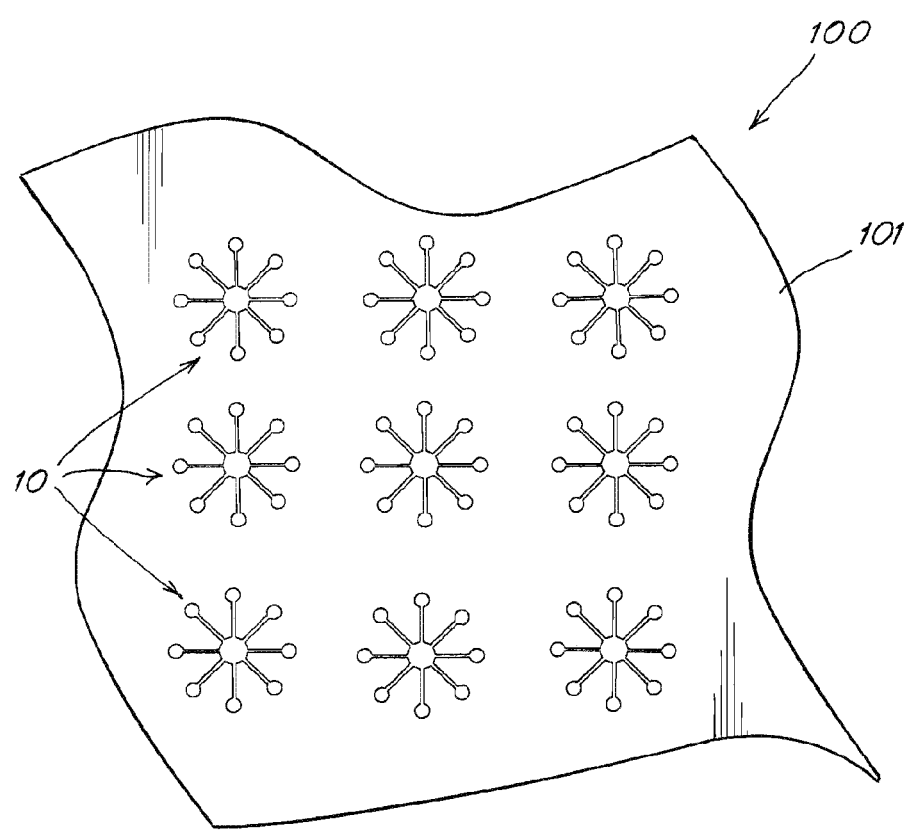
FIG. 8 is an illustration of a tissue gripping layer having an aligned array of tissue gripping elements.

As discussed above, the tissue gripping layer may include a plurality of tissue gripping elements. The tissue gripping elements may be positioned at the tissue gripping layer in many different ways. In one illustrative embodiment, shown in FIG. 3, the tissue gripping elements 10 are arranged in a non-uniform manner, e.g., with non-uniform density of the tissue gripping elements such that the spacing between tissue gripping elements varies. In another illustrative embodiment, shown in FIG. 8, the tissue gripping elements 10 are arranged in an aligned array.

Figure 9:
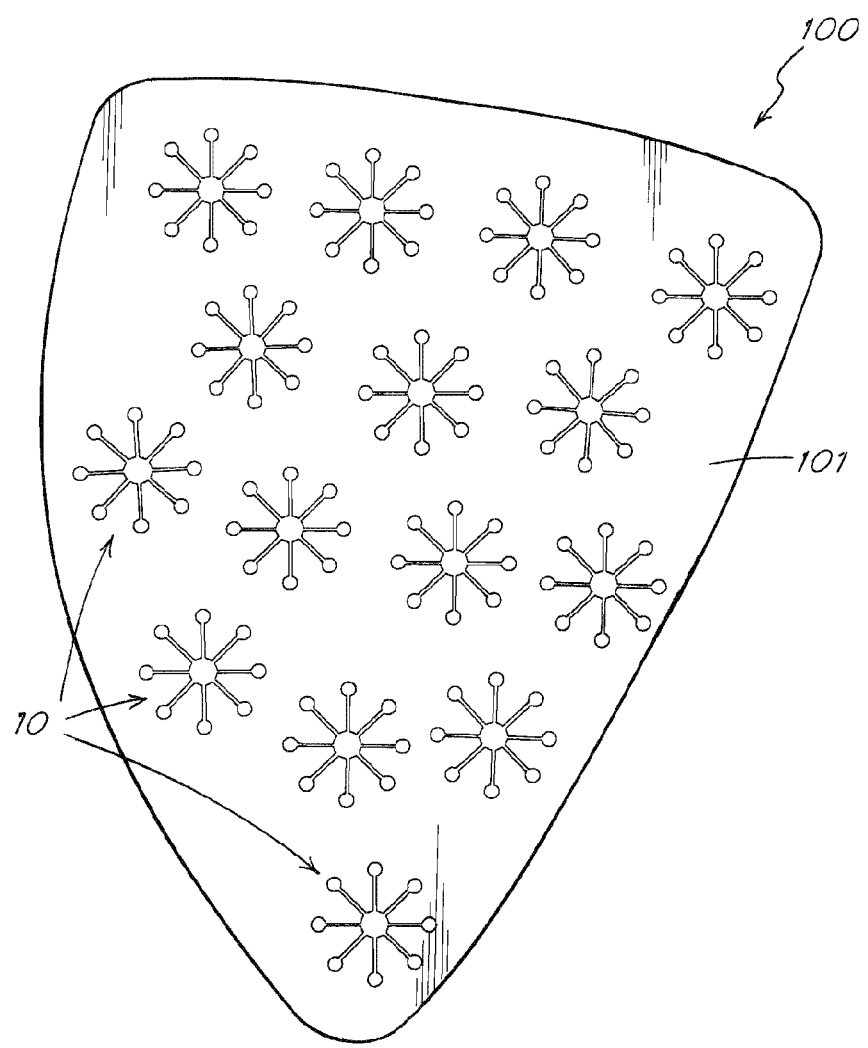
FIG. 9 is an illustration of a shaped tissue gripping layer according to one embodiment.
Figure 10A:
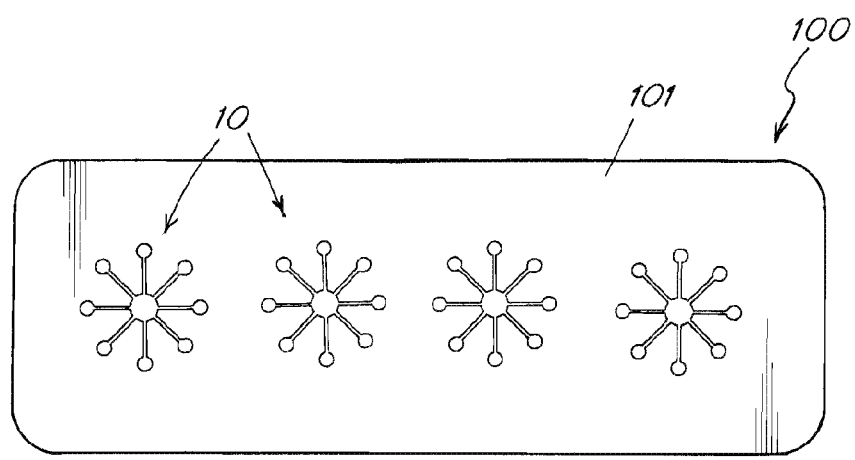
FIG. 10A is an illustration of a shaped tissue gripping layer according to another embodiment.
Figure 10B:
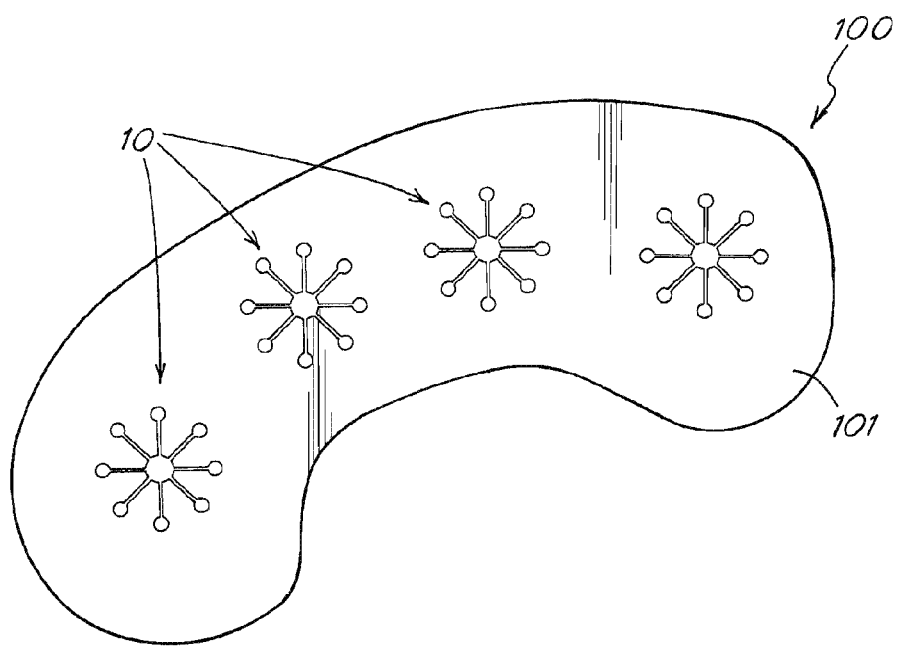
FIG. 10B is an illustration of a shaped tissue gripping layer according to another embodiment.

In some embodiments, the outer perimeter of the tissue gripping layer may be specifically shaped to better fit with the anatomy of the implantation site and/or may be shaped to be used specifically with a certain sized/shaped surgical mesh. As discussed above, the surgical mesh layer and/or the tissue gripping layer may have a three-dimensional contour or other three-dimensional shape for an improved fit with the anatomy of the implantation site. In one illustrative embodiment shown in FIG. 9, the tissue gripping layer 100 is generally triangular in shape, having three sides and three corners. The sides may be curved into arcs and the corners may be rounded. The sides may be equal in length or different. In another illustrative embodiment, shown in FIG. 10A, the tissue gripping layer 100 is generally rectangular in shape, having four sides and four corners. The sides may be curved into arcs and the corners may be rounded. The tissue gripping layer may include tissue gripping elements 10 that are aligned in a linear arrangement. In yet another embodiment, shown in FIG. 10B, the tissue gripping layer 100 has a generally kidney bean shape. The tissue gripping layer may include tissue gripping elements 10 that are arranged in a curved arrangement. The outer perimeter of the tissue gripping layer may be substantially triangular, rectangular, square, pentagonal, hexagonal, circular, elliptical, polygonal, irregular, or any other suitable shape.

According to one aspect, the tissue gripping layer may be separated into more than one portion. In one illustrative embodiment, shown in FIG. 11, the tissue gripping layer is comprised of a plurality of tissue gripping layer portions 110. Each tissue gripping layer portion 110 includes a base 101 and at least one tissue gripping element. In other embodiments, a tissue gripping layer portion may include more than one tissue gripping element. The tissue gripping layer portions 110 may be distributed about the surgical mesh layer at different locations. The tissue gripping layer portions 110 may be uniformly or non-uniformly placed about the surgical mesh layer 200.

The tissue gripping element(s) may be sterilized such that the element(s) is implantable within a human or animal body. Any portion of the prosthesis, or the entire prosthesis, may be sterilized such that the prosthesis is implantable within a human or animal body. Any suitable sterilization process suitable for the desired application may be used as should be apparent to one of skill in the art.

Figure 11:
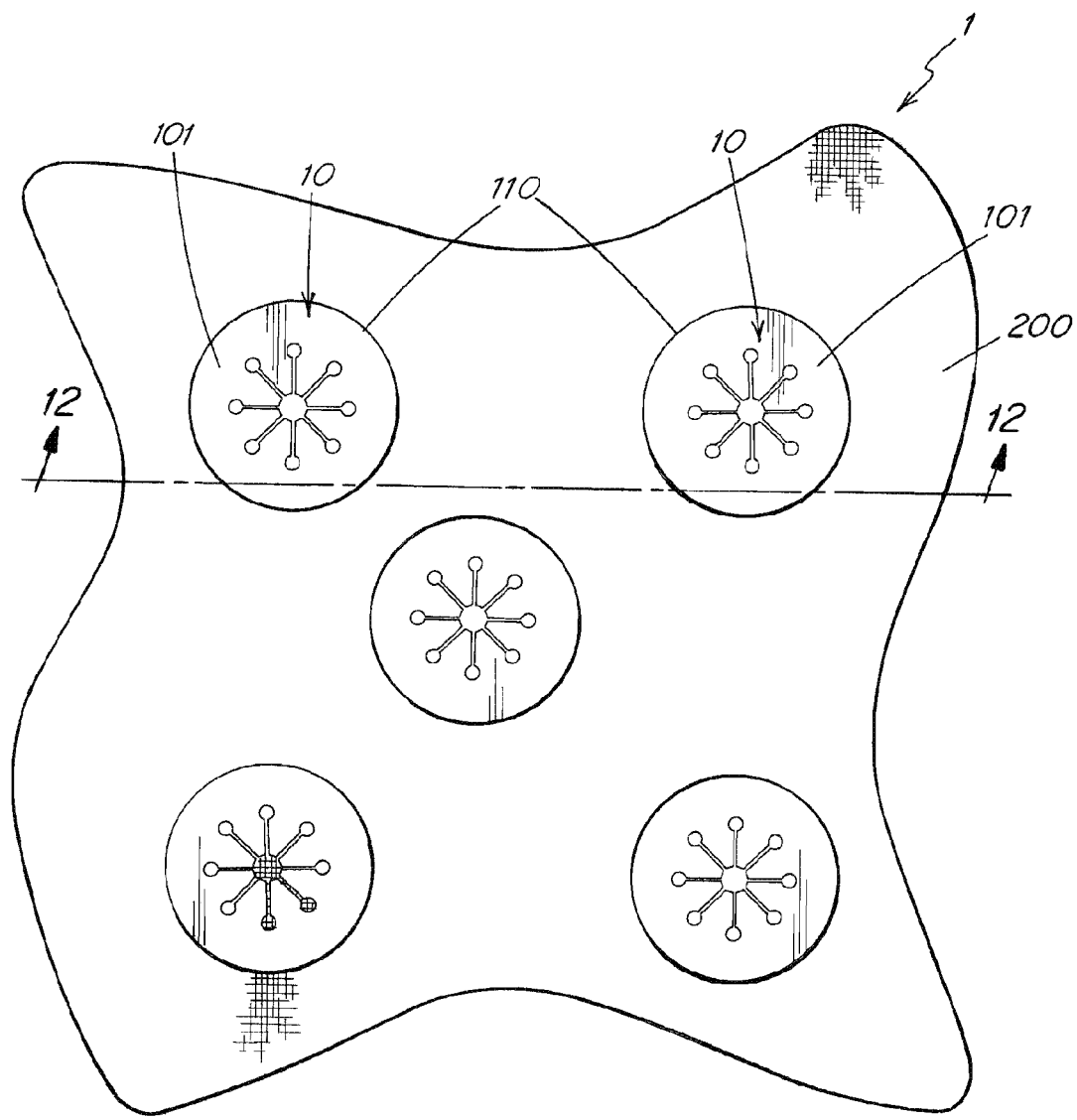
FIG. 11 is an illustration of a prosthesis having a tissue gripping layer comprised of separated portions.
Figure 12:
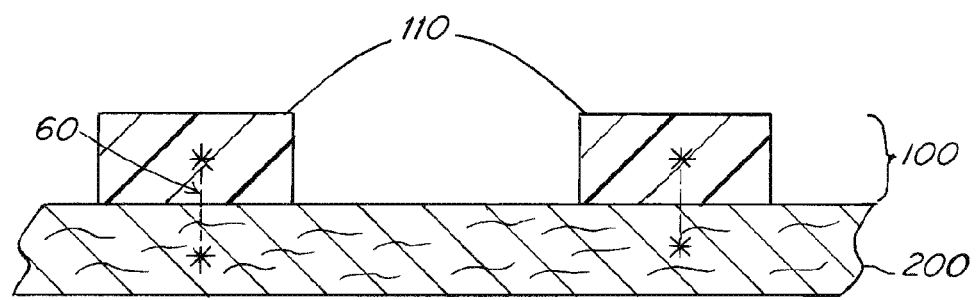
FIG. 12 is a cross-sectional view of the prosthesis shown in FIG. 11 taken along line 12-12.

FIG. 12 depicts a cross-sectional view of the prosthesis 1 through line 12-12 of FIG. 11. As seen in FIG. 12, stitches 60 attach the tissue gripping layer portions 110 to the surgical mesh layer 200. The tissue gripping layer portions may be attached to the surgical mesh layer via any of the attachment arrangements between the surgical mesh layer and the tissue gripping layer that were previously discussed. As also seen in FIG. 12, the tissue gripping layer portions 110 make up the tissue gripping layer 100 even though the tissue gripping layer portions are spaced from one another.

Figure 13:
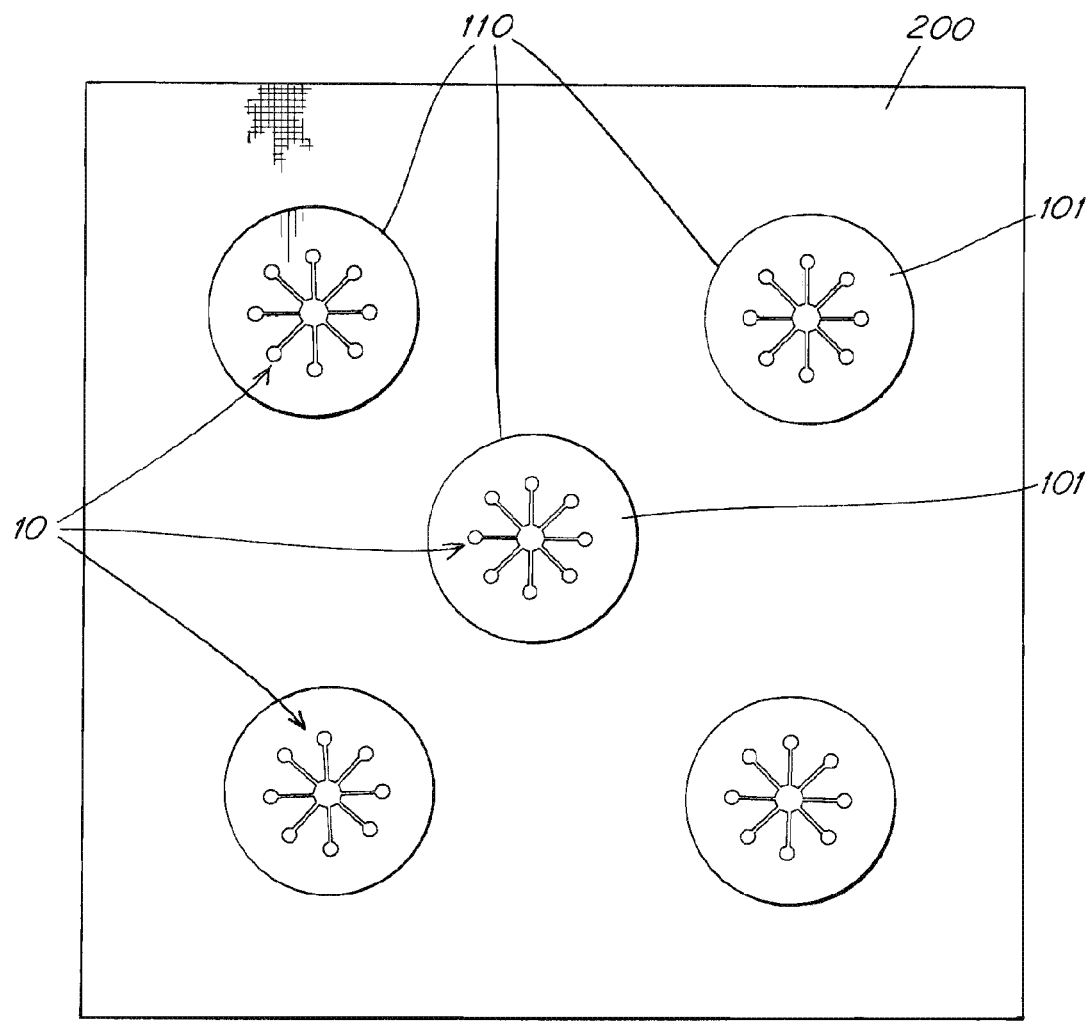
FIG. 13 is an illustration of a prosthesis according to one embodiment.

In another illustrative embodiment, shown in FIG. 13, a plurality of tissue gripping layer portions are distributed across a square or rectangular shaped surgical mesh layer 200. It should be appreciated that, although tissue gripping layer portions are shown having a circular shape, other shapes are possible. Tissue gripping layer portions may be substantially triangular, rectangular, square, pentagonal, hexagonal, circular, elliptical, polygonal, irregular, or any other suitable shape.

Figure 14:
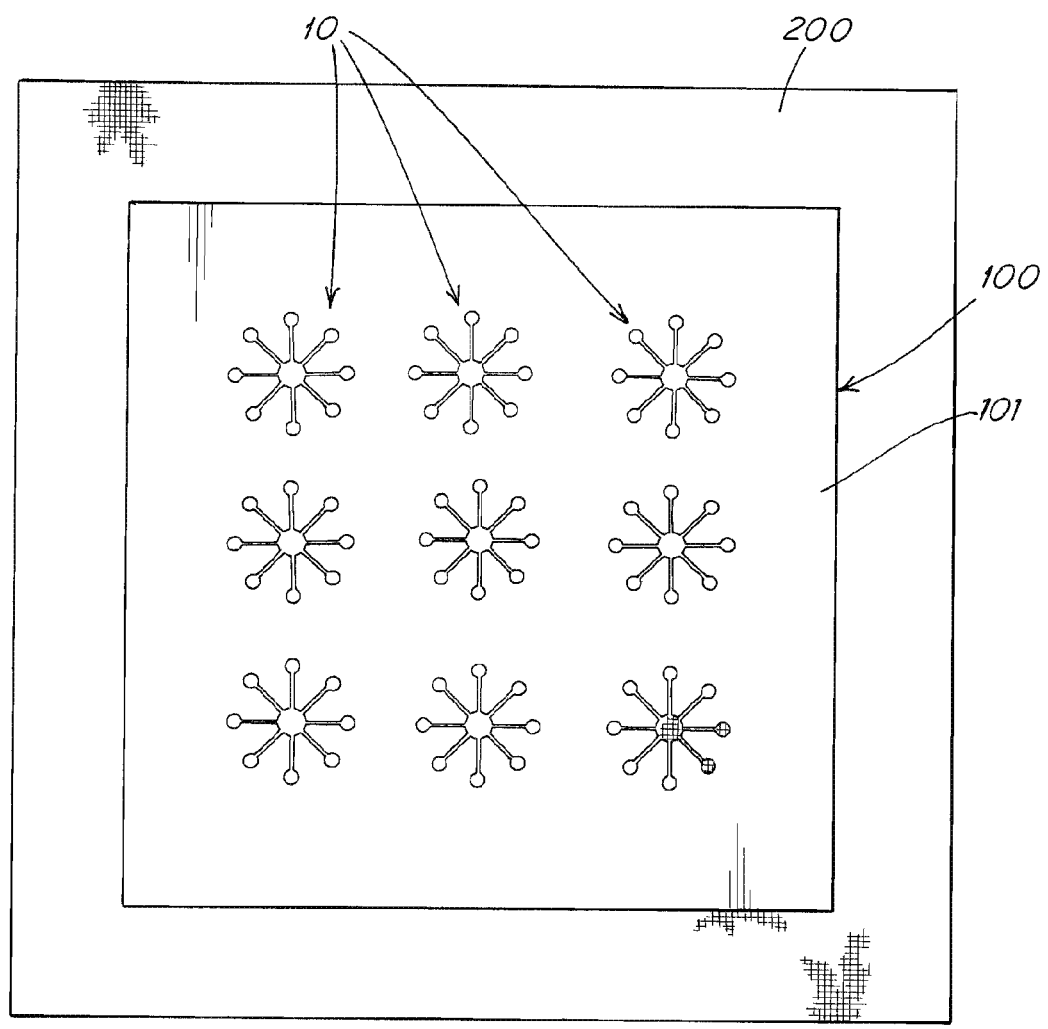
FIG. 14 is an illustration of a prosthesis according to another embodiment.

As discussed above, the tissue gripping layer may have a smaller area than that of the surgical mesh layer. In one illustrative embodiment shown in FIG. 14, the tissue gripping layer 100 has a smaller area than that of the surgical mesh layer 200 such that a border of surgical mesh surrounds the tissue gripping layer. In some embodiments, the tissue gripping layer and the surgical mesh layer may have the same shape such that the border of surgical mesh around the tissue gripping layer is uniform in width. Such an arrangement may be reversed such that the tissue gripping layer has a larger area than that of the surgical mesh layer.

Figure 15:
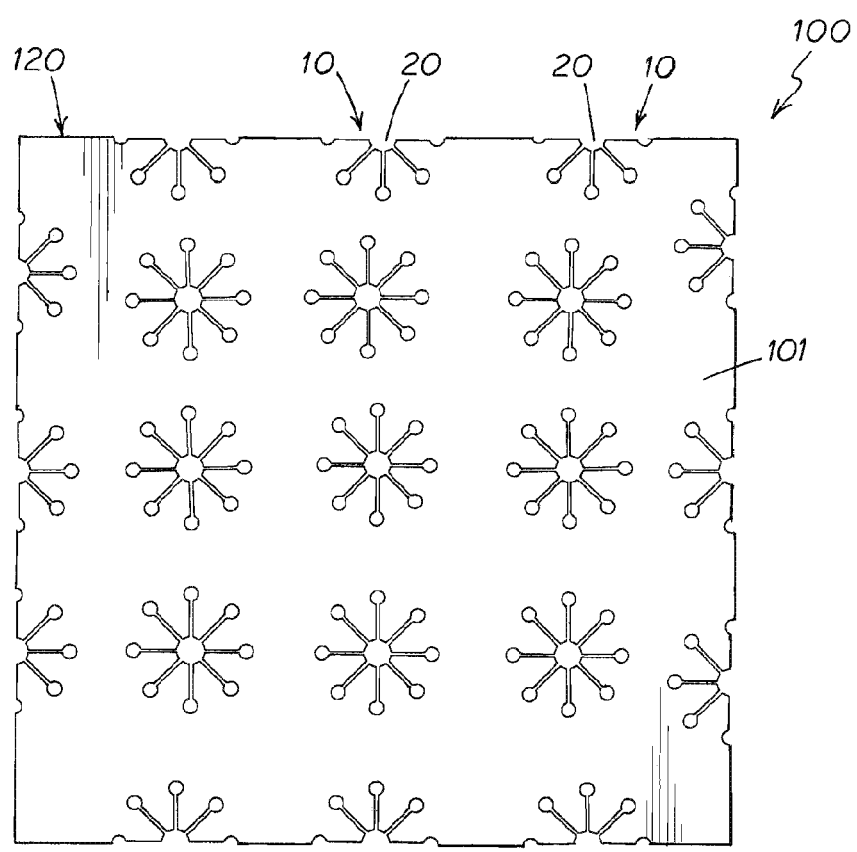
FIG. 15 is an illustration of a tissue gripping layer having tissue gripping elements positioned at the border of the tissue gripping layer.

According to one aspect, one or more tissue gripping elements may be located at the border of a tissue gripping layer. For example, in the illustrative embodiment shown in FIG. 15, tissue gripping elements 10 are located at the border 120 of the tissue gripping layer. The principal opening 20 of a tissue griping element may be only partially surrounded by material.

Figure 16A:
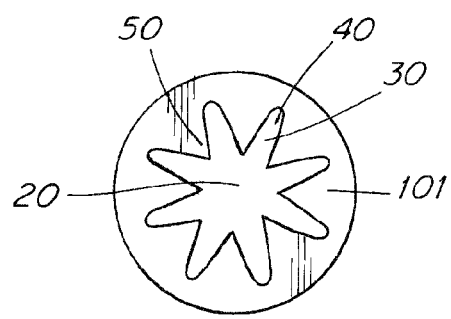
FIG. 16A is an illustration of a tissue gripping element according to one embodiment.
Figure 16B:
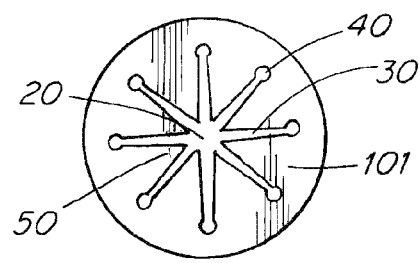
FIG. 16B is an illustration of a tissue gripping element according to another embodiment.
Figure 16C:
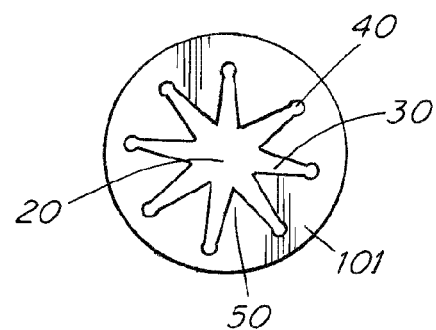
FIG. 16C is an illustration of a tissue gripping element according to another embodiment.

Different tissue gripping element geometries will now be discussed. As discussed previously, the tissue gripping element may include one or more slits. The slits may have uniform width along the entire length of the slit, for example, the slits 30 seen in FIGS. 4-7. However, it should be appreciated that other slit geometries are possible. The tissue gripping element may include a slit that is tapered, may have a width that is wider or narrower than what is shown in FIGS. 4-7, may have a non-uniform width along the length of the slit, may be triangular, elliptical, or any other suitable shape. In the illustrative embodiments shown in FIGS. 16A-16C, the slits 30 are tapered. The first end of the slit 30, which is adjacent to the primary opening 20, is wider than the second end of the slit.

If relief openings 40 are included, the second end of the slit 30 is adjacent to its corresponding relief opening. In some embodiments, the relief opening 40 is smaller than the width of the slit 30 at any point along the length of the slit, such as in the illustrative embodiment shown in FIG. 16A. In some embodiments, the relief opening 40 is wider than the width of the slit 30 at any point along the length of the slit. In some embodiments, the relief opening is wider than the width of the slit 30 at the second end of the slit, but is narrower than the width of the slit at the first end of the slit. The slits and principal opening of the tissue gripping element may form a star-like pattern, such as the patterns shown in FIGS. 16A-16C.

The slit(s) may have a length of 4 to 12 mm or any other suitable length. In some embodiments, the slits may have a negligible width. With a tapered slit, the wide end of the slit may have a width of 1 to 5 mm, or any other suitable width. The narrow end of the slit may have a width of 0.1 to 1 mm, or any other suitable width. The tab(s) may have a length of 4 to 12 mm or any other suitable length. The tabs may have a wide end having a width of about 4 to 12 mm, or any other suitable width, and a narrow end having a width of about 1 to 4 mm, or any other suitable width. In some embodiments, the narrow end of the tab is a point with negligible width. The relief opening may have a diameter of 0.5 to 3 mm, or any other suitable diameter. The primary opening may have a diameter of 1 to 7 mm prior to actuation of the tissue gripping element, or any other suitable diameter.

The inventors have appreciated that some repair surgical meshes used in laparoscopic procedures do not undergo complete expansion upon arrival at the implantation site. According to one aspect, the tissue gripping layer of the prosthesis facilitates expansion of the repair surgical mesh upon arrival at the implantation site. In a laparoscopic procedure or other minimally invasive procedure, the prosthesis is rolled up, folded, collapsed or otherwise in reduced to a compact form to facilitate insertion. Once the prosthesis reaches the implantation site, the prosthesis is unfurled, unfolded, unrolled, or otherwise expanded. The tissue gripping layer facilitates complete expansion of the prosthesis due to the tissue gripping layer's resiliency and/or due to shape memory materials used in the tissue gripping layer.

The implantable prosthesis may include any surgical mesh suitable for repair or augmentation of a soft tissue defect. Without limiting the foregoing, the surgical mesh may constitute a resorbable material, a permanent material, or a hybrid of resorbable and permanent materials. Non-limiting examples of resorbable materials include resorbable polyesters such as polyglycolic acid (PGA), polylactic acid (PLA), poly(lactic-co-glycolic acid) (PLGA), polydioxanone (PDO), polycaprolactone (PCL), any other resorbable polyester, polyhydroxyalkanoate (PHA), as well as collagen, calcium alginate and combinations of any of the foregoing. Permanent materials may include polypropylene, polyethylene, polyester, polytetrafluoroethylene, and other non-resorbable polymers having application in soft tissue repair fabrics. Some or all of the implantable prosthesis may be configured to promote tissue ingrowth into interstices of the implantable prosthesis and/or around the implantable prosthesis, or to discourage same. Thus, the implantable prosthesis may include porous, micro-porous, or essentially non-porous regions, and different regions of the implantable prosthesis may have different porosity characteristics. If desired, some or all of the surfaces of the surgical mesh may include a barrier that is resistant to adhesions with sensitive organs or tissue. The implantable prosthesis may be loaded with one or more medicinal or therapeutic agents including, but not limited to, an analgesic or antibiotic. The implantable prosthesis may be formed of one or more layers, with the layers having the same or different properties including, but not limited to, material composition. The implantable prosthesis may be in the form of a planar-like sheet, and may be configured with convexity, concavity, a combination of convexity and concavity, and may be in the form of other shapes including 3-dimensional shapes. The surgical mesh may be in the form of a 3DMAX Mesh or 3DMAX Light Mesh (Davol Inc.).

In some embodiments, the tissue gripping layer is made of a gelatin material, a surgical mesh or a film, any of which may be absorbable, non-absorbable, or partially absorbable. The tissue gripping layer may include shape memory material that help the tissue gripping layer return to or retain a pre-defined form once the prosthesis reaches the implantation site. In some embodiments, the tissue gripping layer has a higher resiliency and/or stiffness than that of the surgical mesh layer. In some embodiments, the tissue gripping layer may have a thickness of 0.05 to 0.3 mm.

The above aspects and embodiments may be employed in any suitable combination, as the present invention is not limited in this respect.

It should also be understood that, unless clearly indicated to the contrary, in any methods claimed herein that include more than one step or act, the order of the steps or acts of the method is not necessarily limited to the order in which the steps or acts of the method are recited.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A prosthesis that is securable to soft tissue, the prosthesis comprising:
    a surgical mesh; and
    a tissue gripper that is constructed and designed to grip soft tissue to attach the surgical mesh to the soft tissue, the tissue gripper being attached to the surgical mesh, wherein the tissue gripper comprises:
    a base having an outer perimeter;
    a first slit formed through the base, the first slit being defined by at least two portions of the base, the first slit extending in a direction from the outer perimeter toward a reference point, the first slit including a first end located adjacent the reference point and a second end located adjacent the outer perimeter, the first slit having a length and a width;
    a first relief opening positioned at the second end of the first slit, the first relief opening being distinct from and larger than the width of the first slit, the first relief opening being smaller than the length of the first slit;
    a second slit formed through the base, the second slit extending in a direction from the outer perimeter toward the reference point;
    a third slit formed through the base, the third slit extending in a direction from the outer perimeter toward the reference point;
    a first tab defined between the first and second slits, the first tab being moveable away from the surgical mesh into a tissue gripping configuration in response to the application of force; and
    a second tab defined between the second and third slits, the second tab being moveable away from the surgical mesh into a tissue gripping configuration in response to the application of force;
    wherein the base has a planar configuration when the surgical mesh is arranged in a planar configuration, each of the first tab and the second tab being coplanar with the base in the planar configuration prior to actuation of the tissue gripper by the application of force,
    and wherein in response to an application of force to actuate the tissue gripper, tissue is gripped between the at least two portions of the base.

2. The prosthesis of claim 1, wherein the tissue gripper further comprises:
    a third tab defined between the third and first slits, the third tab being moveable away from the surgical mesh into a tissue gripping configuration in response to the application of force.

3. The prosthesis of claim 1, further comprising second and third relief openings corresponding to the second and third slits, respectively, wherein:
  each of the second and third slits has a first end and a second end, and
  for each slit, the corresponding relief opening is positioned at the second end.

4. The prosthesis of claim 1, wherein the base of the tissue gripper is made of a film material.

5. The prosthesis of claim 1, further comprising a tissue gripping layer that includes the tissue gripper.

6. The prosthesis of claim 5, wherein the tissue gripping layer includes a plurality of tissue grippers.

7. The prosthesis of claim 1, wherein the tissue gripper further comprises a primary opening through the base prior to actuation of the tissue gripper, the primary opening being located at the reference point.

8. The prosthesis of claim 7, wherein the primary opening is positioned at a pre-actuation position prior to actuation of the tissue gripper and the first tab is moveable relative to the pre-actuation position of the primary opening.

9. The prosthesis of claim 1, wherein the width of the first slit is uniform along the length thereof.

10. A pressure actuated body tissue gripper for an implantable prosthesis, the pressure actuated body tissue gripper comprising:
  a base having an outer perimeter;
  a first slit being defined by at least two portions of the base, the first slit extending in a direction from the outer perimeter toward a reference point, the first slit including a first end located adjacent the reference point and a second end located adjacent the outer perimeter, the first slit having a length and a width;
  a first relief opening positioned at the second end of the first slit, the first relief opening being distinct from and larger than the width of the first slit, the first relief opening being smaller than the length of the first slit;
  a second slit formed through the base, the second slit extending in a direction from the outer perimeter toward the reference point;
  a third slit formed through the base, the third slit extending in a direction from the outer perimeter toward the reference point;
  a first tab defined between the first and second slits, the first tab being moveable relative to the base into a tissue gripping configuration in response to the application of force,
  a second tab defined between the second and third slits, the second tab being moveable relative to the base into a tissue gripping configuration in response to the application of force; and
  wherein the base has a planar configuration prior to actuation of the tissue gripper by the application of force, each of the first tab and the second tab being coplanar with the base in the planar configuration prior to actuation of the tissue gripper,
  wherein the tissue gripper is sterilized and implantable and is constructed and designed to grip soft tissue.

11. The pressure actuated body tissue gripper of claim 10, further comprising:
  a third tab defined between the third and first slits, the second and third tabs being moveable relative to the base into a tissue gripping configuration in response to pressure actuation.

12. The pressure actuated body tissue gripper of claim 11, further comprising a primary opening through the base prior to actuation of the tissue gripping element.

13. The pressure actuated body tissue gripper of claim 12, wherein the first, second and third slits are directed radially outwardly from the primary opening.

14. The pressure actuated body tissue gripper of claim 10, wherein the base comprises a sheet of material.

15. A prosthesis that is securable to soft tissue, the prosthesis comprising:
  a surgical mesh; and
  a tissue gripping layer which is fabricated separate from and attached to the surgical mesh, the tissue gripping layer including a plurality of tissue grippers constructed and designed to grip soft tissue to attach the surgical mesh to the soft tissue,
  wherein each tissue gripper comprises:
  a base having an outer perimeter;
  a first slit formed through the base, the first slit being defined by at least two portions of the base, the first slit extending in a direction from the outer perimeter toward a reference point, the first slit including a first end located adjacent the reference point and a second end located adjacent the outer perimeter, the first slit having a length and a width; and
  a first relief opening positioned at the second end of the first slit, the first relief opening being distinct from and larger than the width of the first slit, the first relief opening being smaller than the length of the first slit,
  and wherein in response to an application of force to actuate the tissue gripper, tissue is gripped between the at least two portions of the base.

16. The prosthesis of claim 15, wherein the tissue gripper further comprises a second slit formed through the base, the second slit extending in a direction from the outer perimeter toward the reference point; and
  a first tab defined between the first and second slits, the first tab being moveable away from the surgical mesh into a tissue gripping configuration in response to the application of force.

17. The prosthesis of claim 16, wherein the tissue gripper further comprises a third slit formed through the base, the third slit extending in a direction from the outer perimeter toward the reference point.

18. The prosthesis of claim 17, wherein the tissue gripper further comprises:
  a second tab defined between the second and third slits; and
  a third tab defined between the third and first slits, the second and third tabs being moveable away from the surgical mesh into a tissue gripping configuration in response to the application of force.

19. The prosthesis of claim 18 wherein the base has a planar configuration when the surgical mesh is arranged in a planar configuration, each of the tabs being coplanar with the base in the planar configuration prior to actuation of the tissue gripper by the application of force.

20. The prosthesis of claim 15, wherein the width of the first slit is uniform along the length thereof.

21. The prosthesis of claim 17, further comprising second and third relief openings corresponding to the second and third slits, respectively, wherein:
  each of the second and third slits has a first end and a second end, and
  for each slit, the corresponding relief opening is positioned at the second end.

22. The prosthesis of claim 17, wherein the tissue gripper further comprises a primary opening through the base prior to actuation of the tissue gripper, the primary opening being located at the reference point.

23. The prosthesis of claim 22, wherein the primary opening is positioned at a pre-actuation position prior to actuation of the tissue gripper and the first tab is moveable relative to the pre-actuation position of the primary opening.

24. The prosthesis of claim 15, wherein the base of the tissue gripper is made of a film material.

* * * * *